United States Patent [19]

Lok et al.

[11] Patent Number: 4,597,908

[45] Date of Patent: Jul. 1, 1986

[54] PROCESS FOR HYDROGENATING FATTY COMPOUNDS BY USE OF A TRANSITION METAL/TRANSITION METAL SILICATE CATALYST

[75] Inventors: Cornelis M. Lok, Rockanje; Keshab L. Ganguli, Bleiswijk, both of Netherlands

[73] Assignee: Internationale Octrooi Maatschappij "Octropa" B.V., Rotterdam, Netherlands

[21] Appl. No.: 778,687

[22] Filed: Sep. 23, 1985

Related U.S. Application Data

[62] Division of Ser. No. 678,798, Dec. 5, 1984.

[30] Foreign Application Priority Data

Dec. 6, 1983 [NL]  Netherlands ................ 8304184

[51] Int. Cl.$^4$ ................ C11C 3/12; B01J 23/70; B01J 21/08; C07C 85/12
[52] U.S. Cl. ................ 260/409; 564/490; 260/690; 502/244; 502/259; 502/260
[58] Field of Search ............ 502/244, 259, 260; 260/409, 690; 564/490

[56] References Cited

U.S. PATENT DOCUMENTS

| | | | |
|---|---|---|---|
| 2,392,107 | 1/1946 | Teter | 502/260 |
| 2,643,266 | 6/1953 | Teter | 502/260 |
| 2,783,286 | 2/1957 | Reynolds | 502/244 |
| 3,598,759 | 8/1971 | Bertolacini | 502/259 |
| 4,184,982 | 1/1980 | Schroeder et al. | 502/260 |
| 4,307,248 | 12/1981 | Barnett et al. | 260/409 |
| 4,532,351 | 7/1985 | Barnett et al. | 260/409 |

FOREIGN PATENT DOCUMENTS

| | | | |
|---|---|---|---|
| 0206161 | 1/1984 | Fed. Rep. of Germany | 260/409 |
| 2105604 | 3/1983 | United Kingdom | 502/259 |

*Primary Examiner*—Anton H. Sutto
*Assistant Examiner*—Elizabeth A. Flaherty
*Attorney, Agent, or Firm*—Cushman, Darby & Cushman

[57] ABSTRACT

The invention provides a process for the preparation of a transition metal-silicate catalyst in which an insoluble, basic compound of a transition metal having an atomic number between 26 and 30 (in particular nickel which has an atomic number of 28) is rapidly precipitated with an alkaline precipitation agent from an aqueous solution of such a metal salt, as a suspension, which precipitate is allowed to mature for a longer period in a suspended form, and, after the transition metal ions have been practically completely precipitated, soluble silicate is added to the suspension, after which the solids are separated from the liquid, optionally washed, dried and reduced.

2 Claims, No Drawings

PROCESS FOR HYDROGENATING FATTY COMPOUNDS BY USE OF A TRANSITION METAL/TRANSITION METAL SILICATE CATALYST

This is a continuation, division, of application Ser. No. 678,798 filed Dec. 5, 1984.

The application relates to a process for preparing a transition metal-silicate catalyst in which an insoluble, basic compound of a transition metal having an atomic number between 26 and 30 is precipitated from an aqueous solution of a transition metal salt as a suspension, which precipitate is allowed to mature in suspended form and is subsequently separated, dried and reduced. These catalysts are used especially in the hydrogenation of unsaturated compounds, particularly fatty acids and their derivatives such as triglycerides and nitriles.

It is known in the art to co-precipitate nickel ions with an alkaline precipitating agent and silicate. Such a process is disclosed in German "Auslegeschrift" (DE-B) No. 2 150 975 (Esso). According to this process nickel ions and silicate ions are co-precipitated from a solution onto a porous silicon dioxide carrier with an alkaline precipitation agent, such as for example ammonium carbonate. The catalyst so obtained, however, has certain disadvantages as to certain properties; in particular filtration often causes difficulties.

It has now been found that when, after the metal ions are practically completely precipitated by addition of the alkaline agent, soluble silicate is added to the suspension and this suspension is allowed to mature further, better catalysts can be obtained. In particular, a catalyst is then obtained having a particularly favourable combination of activity and selectivity. The filtration properties also compare particularly favourably with those of the aforementioned, known (co-precipitation) catalysts. With the new process, generally there is no carrier material present during the precipitation.

The added soluble silicate reacts in the maturing reactor with the excess of basic ions still present, forming insoluble metal silicate. The transition metals which can be used in the practice of this invention are cobalt (atomic number 27), nickel (atomic number 28) and copper (atomic number 29). In the practice of the prent invention nickel catalysts are preferred.

The addition of a soluble silicate should take place as quickly as possible after precipitation of the metal, preferably within 30 minutes, more particularly within 15 minutes.

The amount of soluble silicate which is added is 0.1 to 0.6 moles, preferably 0.2 to 0.4 moles per mole of metal in the suspension.

In comparison with the catalysts for which the transition metal is co-precipitated according to the prior art in the presence of dissolved silicate, the catalysts according to the invention have a distinctly improved activity, selectivity and filtrability, the last-mentioned being of great technical importance both when manufacturing the catalyst and when using the catalysts (particularly for the separation of the catalyst after the hydrogenation).

Also, there are indications that catalyst particles obtained according to the present invention have somewhat large rounded, cauliflower-type shapes, as a result of which the catalyst can also be filtered better, also in the reduced form. Properties of this catalyst, such as the improved combination of hydrogenating activity and selectivity also show that, because of the addition of soluble silicate only after the metal ions have practically been precipitated and the catalyst subsequently is allowed to mature, favourable changes in structure and composition of the catalyst take place. The catalysts according to the present invention are characterized by an active metal content of 30 to 70% by weight, a specific nickel surface area of 100 to 160 $m^2/g$ nickel or 1–25 $m^2/g$ in the case of copper or cobalt, and an $SiO_2$ to metal molar ratio between 0.2 and 0.4, as well as a high pore volume and a high filtration speed which is at least five times the filtration speed found for a coprecipitated catalyst of similar composition.

The catalysts according to this invention may contain a water-soluble carrier material which was already present during the preparation or was added thereafter. Suitable carrier materials are e.g. silica-containing substances such as kieselguhr, aluminum trioxide, and silicates such as bentonite. Kieselguhr is preferred, particularly kieselguhr containing 50–90% by weight of amorphous silica. According to the present invention, however, preferably no insoluble carrier is used. Nevertheless, for special applications the presence of an insoluble carrier can be desirable. If carrier material is used, this carrier material may be added (a) direct as such, (b) as an aqueous suspension, (c) preferably as a suspension in an aqueous solution of a metal salt, or (d) as a suspension in an aqueous solution of the alkaline substance.

According to embodiments (a) to (d) this carrier material may be added before or during the precipitation. According to embodiment (a), (b) or (d) the carrier may, however, be added completely or partly (preferably the latter) after the precipitation, but also before or during the maturing.

After precipitation and maturing, according to the invention the solids are separated from the liquid, if required washed, dried and activated (=reduced) by bringing them into contact with hydrogen at elevated temperature, this in a manner better known per se.

Transition metal compounds which may be used as starting material for the preparation of the catalysts according to this invention are water-soluble metal compounds such as nitrate, sulphate, acetate, chloride and formate of the metals nickel, copper and cobalt. The solutions which are fed into the precipitation reactor preferably contain between 10 and 80 grams of metal per liter; particularly preferred are solutions which contain between 25 and 60 g metal per liter.

Alkaline precipitation agents which can be used as starting material for the process of preparation according to the present invention are alkali metal hydroxides, alkali metal carbonates, alkali metal bicarbonates, the corresponding ammonium compounds and mixtures of the above-mentioned compounds. The concentration of the alkaline solution which is fed into the precipitation reactor is preferably 20 to 300 g basic material (calculated as anhydrous material) per liter (in so far as the solubility permits that), more particularly between 50 and 250 g per liter.

It has turned out to be appropriate to use both solutions (the one containing the transition metal and the one containing the alkaline precipitation agent) in approximately equal concentrations expressed in equivalents, so that also almost equal volumes are reacted Preferably a stoichiometric excess of alkali is used. Normally the process is carried out in an aqueous medium.

The transition metal-containing solution and the alkaline solution are added in such amounts per unit of time that during the precipitation step there is a small exess of alkaline compound present.

As a rule the precipitation reactor contains a device for vigorously agitating the liquid and the reactor is of such a dimension with respect to the amounts of liquid pumped in that short average residence times can be obtained. Average residence times in the precipitation reactor between 0.1 sec. and 30 minutes, preferably between 0.2 sec. and 10 minutes, more preferably less than 2 minutes, are applied as a rule. The precipitation step and also the maturing step may be carried out batchwise (=discontinuously), continuously and semi-continuously (e.g. according to the cascade method).

In a preferred embodiment, in which the precipitation step (step 1) is carried out continuously, the amounts of solutions to be fed into the precipitation reactor are dosed by measuring, optionally continuously, the alkalinity (normality) of the discharged liquid. This can also be dosed by pH determination (pH 7,0–10). The temperature at which the precipitation takes place (2°–60° C.) can conveniently be adjusted by regulating the temperatures of the solutions fed in. The vigorous agitation of the liquid in the precipitation reactor preferably takes place with a mechanical energy input between 5 and 2000 Watts per kg of solution (jet mixing being prefered).

The reaction mixture (suspension) which is obtained from the precipitation reactor goes immediately thereafter into a significantly larger post-reactor, in which the suspension is kept agitated and is matured. Here soluble silicate and possible other compounds are added, such as carrier material, alkaline solution as described above and/or possibly promotors. The amount of silicate added is 0.1 to 0.6, preferably 0.2 to 0.4 moles of silicate per mole of metal in the suspension. Preferably alkali silicate is added, more especially sodium silicate, and neutral silicate such as $Na_2O.3\ SiO_2$ is preferred. Preferably, the liquid in the post-reactor(s) during the maturing step, is kept at a temperature between 60° and about 105° C., more preferably between 70° and 90° C.

The normality of the liquid in the post-reactor changes little during the aging step (step 2) but is normally in the same range as during the precipitation step (step 1). As a result of $CO_2$ escaping during the maturing, the alkalinity increases slightly. The maturing step may be carried out in one or more post-reactors during which the (total) average residence time is kept between 5 and 180 minutes, preferbly between 10 and 90 minutes. If two or more post-reactors are used it may be desirable to carry out the process in such a way that in the second or further post-reactors the temperature is different, more in particular between 5 and 15 centigrades lower than that in the first post-reactor.

After the maturing step has been completed, the solid components are separated from the mother liquid, washed if necessary, dried, e.g. in the presence of a surface-active material or organic solvent, e.g. acetone, or by means of spray-drying or freeze-drying. Spray-drying and freeze-drying are preferred because they generally result in better catalytic properties. The separated solid material is preferably washed with water; sometimes the washing water is made lightly alkaline and/or there is a surface-active material incorporated in it. Thereafter, if desired, the dry solid material is ground and/or calcined and then activated with hydrogen gas at an increased temperature, which as a rule lies between 350° and 450° C., preferably between 300° and 400° C. This activation can take place at atmospheric pressure or under increased pressure.

Preferably, before the reduction takes place, or during a step preceding this, promotors can be added in an easy manner. Suitable amounts of promotors are from 0.05 to 10%, calculated on the weight of transition metal, of other transition metals or compounds such as copper, cobalt, molybdenum, silver, magnesium, possibly further metals and combinations thereof.

The catalyst thus obtained is especially suitable for the hydrogenation of unsaturated compounds such as oils, fats, fatty acids, fatty nitriles and other fatty acid derivatives. This hydrogenation is carried out at increased temperature (80°–250° C.) and optionally increased pressure ($1-50.10^5$ $N/m^2$) with hydrogen.

The hydrogenated products thus obtained, e.g. hydrogenated oils, possess a favourable combination of properties, such as low tri-saturated content, sometimes combined with a steep dilatation curve.

EXAMPLE 1

Solutions of $NiSO_4$ (35 g Ni/l) and soda (10% by weight) were continuously pumped at equal rate of flow (25 ml/min$^{-1}$) into a vigorously stirred precipitation reactor, during which nickel hydroxide/carbonate precipitated at a temperature of 20° C. The pH of the suspension in this reactor was 9.4. In this precipitation reactor (capacity 25 ml) in which the precipitation took place, the suspension had an average residence time of 0.5 min. This suspension has transferred continuously to a second, maturing reactor (volume 1500 ml) in which the average residence time was about 30 min. and the temperature was 97° C. Simultaneously, an amount of silicate ions was dosed continuously into this second reactor, in the form of waterglass, at a rate of 0.26 g $SiO_2$/min. The $SiO_2$:Ni ratio was 0.3 on an average (molecular ratio).

The pH of the suspension in the second reactor was 8.8. The liquid level in the second reactor was kept constant by sucking off any excess with the aid of vacuum, as a result of which the indicated residence time was regulated.

After an experiment duration of 90 min. (3×residence time) the maturing was stopped and the contents of the reactor filtered. The green filtercake thus obtained was washed. The washed cake was dried at 120° C. in a drying stove and thereafter activated with hydrogen gas for 30 minutes at a temperature of 400° C. From the determination of the nickel surface area by hydrogen adsorption, it appeared that the catalyst contained nickel crystallites having an average diameter of 2.7 nanometers.

The speed of filtration of the green cake was measured as follows:

1 liter of green cake slurry with 4% solid phase from the maturing reactor was filtered over a Büchner funnel with a Schleicher Schüll black band filter having a diameter of 125 mm.

The vacuum applied was a 2 to 3 cm under-pressure. This vacuum was measured with a manometer and obtained with a water pump. The filtration time in minutes was defined as the time necessary for filtering 4 liters of water over the catalyst bed. This filtration speed is recorded in Table I.

The oil filtration, i.e. after carrying out the hydrogenation, was measured as follows:

After the hydrogenation, the slurry, i.e. the oil and the catalyst, was cooled to 90° C. and pumped to a closed filtering vessel. This is a double-walled vessel connected to a thermostat standing at 90° C. The bottom of this vessel contains a cotton filtering cloth having a diameter of 30 cm. After the oil and the catalyst had been pumped into the filtering vessel an excess pressure of $3.10^5$ N/m² was applied. During the filtration this pressure was maintained with a Kendall pressure regulator. After application of the pressure the filtration time was noted. The filtered oil was collected in a tube under the filtering vessel. The weight of the filtered oil in the tube was noted as a function of time.

Subsequently, the weight of the filtered oil was plotted graphically as the X axis against the time divided by the weight of the oil, and the slope of the line obtained is the criterion for the cake resistance.

The values in min/g for 150 g oil are recorded in Table II.

The selectivity of the catalyst was measured by hydrogenating 250 g fish oil having an iodine number of 165 to an iodine number of 85 with 0.1% Ni catalyst with 60 liters H₂/per hour under a pressure of $1.10^5$ N/m² at 180° C. The hydrogenation time and melting points of the hydrogenated oils were determined. (Cf. Table II.)

The activity of the catalyst in connection with hydrogenation of fish oil ($A_f$) was measured as follows: 150 g fish oil was hydrogenated at 180° C. at an H₂ pressure of $1.10^5$ N/m² with a catalyst dose of 0.15 g Ni. Hydrogenation was carried out until an iodine number of 80 was reached. The decrease in the refractive index was determined and compared with the same hydrogenation with a known standard catalyst and expressed as a percentage. (Cf. Table II.)

EXAMPLES 2-3

Some more catalysts according to the invention were prepared in accordance with the procedure described in Example 1, with, however, variations being made in the amounts and conditions, as appears from Table I.

In Table I and Table II the conditions and the selectivity and activity of these catalysts are recorded.

It is notable that, on an average, shorter hydrogenation times were sufficient and that with fish oil the catalyst also retained its activity longer. A greater selectivity was also observed, i.e. less tri-saturated triglycerides were formed. Finally, the filtration properties of green cake and catalyst after hydrogenation appeared to be particularly favourable, especially when compared with the comparative examples where waterglass was dosed into the precipitation reactor.

TABLE I

| Example | 1 | 2 | 3 |
|---|---|---|---|
| Ni:SiO₂ ratio | 3.33 | 10 | 2.0 |
| Molarity (moles/l) of the soda solution | 1.0 | 1.0 | 1.0 |
| Molarity of the nickel solution | 0.6 | 0.6 | 0.6 |
| Precipitation temperature (°C.) | 20 | 20 | 20 |
| Average precipitation time (min.) | 0.5 | 0.5 | 0.5 |
| pH value | 9.4 | 9.4 | 9.4 |
| Maturing temperature (°C.) | 97 | 97 | 97 |
| pH value | 8.7 | 8.75 | 8.9 |
| Green cake filtration time (min.) | 3 | 2 | 3 |

TABLE II

| Example | 1 | 2 | 3 |
|---|---|---|---|
| Ni % in reduced catalyst | 9 | 70 | 65 |
| Oil hydrogenation test refined fish oil with respect to selectivity Hydrogenation time | | | |
| Acetone, oven drying (min.) | 76 | 350 | 99 |
| Water, oven drying (min.) | 93 | 600 | 200 |
| Melting point oil (°C.) | | | |
| Acetone, oven drying | 30 | 32 | 36 |
| Water, oven drying | 33 | 36 | 40 |
| Green cake | | | |
| $A_f$ test after washing with water (%) | 100 | 75 | 60 |
| $A_f$ test after washing with acetone (%) | 160 | 122 | 120 |
| Filtration after hydrogenation 150 gm oil (min/g) | 0.05 | 0.05 | 0.05 |

COMPARATIVE EXAMPLES 1-3

The preparation and the steps involved therein were carried out in accordance with Example 1. In this case water glass was dosed into the precipitation reactor.

The results are recorded in Tables III and IV.

TABLE III

| | (Preparation) | | |
|---|---|---|---|
| Comparative Example | 1 | 2 | 3 |
| Ni:SiO₂ ratio precipitation | 3.33 | 10 | 2.0 |
| Molarity of the nickel solution | 1.0 | 1.0 | 1.0 |
| Molarity of the nickel solution | 0.6 | 0.6 | 0.6 |
| Precipitation temperature (°C.) | 20 | 20 | 20 |
| Average precipitation time (min.) | 0.5 | 0.5 | 0.5 |
| pH value | 9.5 | 9.4 | 9.3 |
| Temperature (°C.) | 97 | 97 | 97 |
| Green cake filtration time (min.) | 30 | 10 | 55 |

TABLE IV

| Example | 1 | 2 | 3 |
|---|---|---|---|
| Ni:SiO₂ | 3.33 | 10 | 2 |
| Ni % in the activated catalyst | 70 | 70 | 20 |
| $A_f$ test (water-washed) | —* | 54 | —* |
| $A_f$ test (acetone-washed) | —* | 120 | —* |
| Melting point | | | |
| washing with water | —* | 33.5 | —* |
| washing with acetone | —* | 31.0 | —* |
| Oil filtration of 150 g oil (min./g) | 0.9 | 0.85 | 0.8 |

*indicates no determinations made

EXAMPLE 4

Herein the hydrogenation of tallow fatty acid nitrile to amine is described. The catalyst was obtained as described in Example 2. The reaction was carried out in an autoclave of 200 ml, containing with 70 ml tallow fatty acid nitrile (acid number of 0.2) and an amount of catalyst corresponding with 0.18% Ni at a H₂ pressure of $30.10^5$ Pa.

The temperature was 110° C. at the start of the reaction and ran through the reaction heat up to 130° C. It was maintained at that temperature for 2 hours.

The ratio of $N_2$ to $NH_3$ as 1:1. The conversion of the the nitrile was 74%.

The yield of primary amine was 64% and the selectivity towards primary amine 89%.

The selectivity and filtration speed of the catalyst from the hydrogenated mixture were higher than those which were obtained after hydrogenating with the catalyst according to Comparative Example 2.

EXAMPLE 5

Solutions of $Co(NO_3)_2$ (0.6 mole/liter) and soda (10% by weight) were continuously pumped at equal rate of flow (25 ml/min$^{-1}$) into a vigorously stirred precipitation reactor, during which cobalt hydroxide/carbonate precipitated at a temperature of 20° C. The pH of the suspension in this reactor was 9.3. In this precipitation reactor (capacity 25 ml) in which the precipitation took place, the suspension had an average residence time of 0.5 min. This suspension was transferred continuously to a second, maturing reactor (volume 1500 ml) in which the average residence time was about 30 min. and the temperature was 90° C. Simultaneously, an amount of $SiO_2$ ions was dosed continuously into this second reactor, in the form of waterglass, at a rate of 0.26 g $SiO_2$/min. The $SiO_2$:Co ratio was 0.2 on an average (molecular ratio).

The pH of the suspension in the second reactor was 9.0. The total liquid level in the second reactor was kept constant by sucking off any excess with the aid of vacuum, as a result of which the indicated residence time was also regulated.

After an experiment duration of 90 min. (3×residence time) the maturing was stopped and the contents of the reactor filtered. The purple filtercake thus obtained was washed with water. The washed cake was spray-dried and thereafter activated with hydrogen gas for 30 minutes at a temperature of 450° C. From the determination of the metal surface area with the aid of hydrogen adsorption, yielding a metal surface area of 8.9 m$^2$/g catalyst, it appeared that the catalyst consisted of crystallites having an average diameter of 16.0 nanometers.

The speed of filtration of the purple cake was measured as follows:

1 liter of purple cake slurry with 4% solid phase from the maturing reactor was filtered over a Büchner funnel with a Schleicher Schüll black band filter having a cross-section of 125 mm.

The vacuum applied was a 2 to 3 cm under-pressure. This vacuum was measured with a manometer and reached with a water jet air pump. The filtration time in minutes was defined as the time necessary for filtering 4 liters of water over the catalyst bed. This filtration speed was 14 minutes.

The activity of the cobalt-silicate catalyst thus obtained was tested in the hydrogenation reaction of $C_{18}$ nitriles to amines.

To this end an amount of activated Co-silicate catalyst, corresponding with an amount of Co metal of 0.18% and 0.12% (based on the weight of the nitrile) was added to the nitrile.

The reaction was carried out in an autoclave in the presence of hydrogen and ammonia of which the partial pressures were each 1.5 M Pa and 2.5 M Pa, respectively. When the uptake of hydrogen ceased the reaction was considered completed. Thereafter the conversion of nitrile into amine and the selectivity towards the primary amine were determined. The conversion to amines was 100%, while the selectivity was 97% and 93%, respectively.

The speed of filtration after the hydrogenation had been completed was determined in a way similar to that described in Example 1 and a value of about 0.1 min/g was obatained.

EXAMPLE 6

Solutions of $CuSO_4$ (0.6 mole/liter) and soda (10% by weight) were continuously pumped at equal rate of flow (25 ml/min$^{-1}$) into a vigorously stirred precipitation reactor, during which copper hydroxide/carbonate precipitated at a temperature of 20° C. The pH of the suspension in this reactor was 8.9. In this precipitation reactor (capacity 25 ml) in which the precipitation took place, the suspension had an average residence time of 0.5 min. This suspension was transferred continuously to a second, maturing reactor (volume 1500 ml) in which the average residence time was about 30 min. and the temperature was 97° C. Simultaneously, an amount of $SiO_2$ ions was dosed continuously into this second reactor, in the form of waterglass, at a rate of 0.26 g $SiO_2$/min. The $SiO_2$:Cu ratio was 0.3 on an average (molecular ratio).

The pH of the suspension in the second reactor was 9.0. The total liquid level in the second reactor was kept constant by sucking off any excess with the aid of vacuum, as a result of which the indicated residence time was also regulated.

After an experiment duration of 90 min. (3×residence time) the maturing was stopped and the contents of the reactor filtered. The blue filtercake thus obtained was washed with water. The washed cake was spray-dried and thereafter activated with hydrogen gas for 30 minutes at a temperature of 250° C. From the determination of the metal surface area with the aid of carbon monoxide chemisorption, yielding an active metal surface area of 3.3 m$^2$/g catalyst, it appeared that the catalyst consisted of crystallites having an average diameter of 16.3 manometers.

The speed of filtration of the blue cake was measured as follows:

1 liter of blue cake slurry with 4% solid phase from the maturing reactor was filtered over a Büchner funnel with a Schleicher Schüll black band filter having a cross-section of 125 mm.

The vacuum applied was a 2 to 3 cm under-pressure. This vacuum was measured with a manometer and reached with a water jet air pump. The filtration time in minutes was defined as the time necessary for filtering 4 liters of water over the catalyst bed. This filtration speed was 2 minutes.

The activity of the copper-silicate catalyst prepared as described above was tested in the hydrogenation reaction of soybean oil.

For this purpose an amount of Cu-silicate catalyst, corresponding with an amount of Cu metal of 0.3% (based on the weight of the soybean oil) was added to the soybean oil. The activation of the Cu-silicate catalyst with the aid of hydrogen took place in situ in the rection vessel during the heating of the reaction mixture to the reaction temperature.

The reaction was carried out in a hydrogenation vessel where, under atmospheric pressure, hydrogen (1 l/min) was stirred through the soybean oil with the aid of a stirring mechanism (3000 revolutions per minute). The reaction was carried out for 1 hour. Hereafter the difference in the refractive index of the starting material (soybean oil) and of the reaction product was determined at a temperature of 65° C. The magnitude of this difference was taken as measure of the activity of the catalyst. (Decrease of $N^{65}{}_D = 1.4580$ to $N^{65}{}_D = 1.4544$.)

The speed of filtration after the hydrogenation had been completed was determined in a way similar to that described in Example 1 and a value of about 0.1 min/g was obtained.

We claim:

1. In a process for the catalytic hydrogenation of unsaturated compounds consisting of oils, fats, fatty acids, fatty nitriles and other fatty derivatives at a temperature between 80° and 250° C., the improvement which comprises using, as the catalyst, a transition metal/transition metal silicate catalyst, which contains 30 to 70% of active metal, calculated on the total weight of the catalyst, wherein the active metal surface area is between 100 and 160 $m^2/g$ in the case of nickel and between 1 and 25 $m^2/g$ in the case of cobalt and copper, and wherein the BET total surface area and the pore volume are at least 20% higher and the filtration speed from the hydrogenated mixture is at least 5×that of a coprecipitated catalyst of the same composition.

2. In a process for the catalytic hydrogenation of unsaturated compounds, the improvement wherein the catalyst utilized is prepared by a process wherein an insoluble, basic compound of a transition metal having an atomic number between 26 and 30 is precipitated with an alkaline precipitation agent from an aqueous solution of such a metal salt, as a suspension, which precipitate is allowed to mature in suspended form and is subsequently separated, dried and reduced, wherein, after the transition metal ions have been practically completely precipitated, soluble silicate is added.

* * * * *